United States Patent

Holm et al.

Patent Number: 5,849,178
Date of Patent: Dec. 15, 1998

[54] APPARATUS FOR SEPARATING A BLOOD COMPONENT FROM BLOOD PLASMA

[75] Inventors: Niels Erik Holm, Birkerød; Glenn A. Jorgensen, Allerod, both of Denmark

[73] Assignee: Bristol-Myers Squibb Company, New York, N.Y.

[21] Appl. No.: 4,408

[22] Filed: Jan. 8, 1998

Related U.S. Application Data

[60] Provisional application No. 60/034,055 Jan. 8, 1997.

[51] Int. Cl.$^6$ ............................. B01D 21/76; G01N 21/01
[52] U.S. Cl. ............................. 210/85; 210/97; 210/109; 210/360.1; 210/380.1; 422/72; 422/82.05; 422/101; 435/3; 435/13; 436/164; 436/177; 494/1; 494/2; 494/3; 494/10; 604/6
[58] Field of Search ............................. 210/85, 94, 97, 210/109, 360.1, 361, 380.1, 739, 745, 782, 787, 789; 494/1, 2, 3, 10, 43; 435/3, 13; 436/164, 177; 422/72, 82.05, 101; 604/6

[56] References Cited

U.S. PATENT DOCUMENTS

| | | | |
|---|---|---|---|
| 3,073,517 | 1/1963 | Pickels et al. . | |
| 3,581,981 | 6/1971 | Latham, Jr. . | |
| 4,151,844 | 5/1979 | Cullis et al. | 210/194 |
| 5,122,284 | 6/1992 | Braynin et al. | 210/782 |
| 5,308,506 | 5/1994 | McEwen et al. | 210/745 |
| 5,387,174 | 2/1995 | Rochat | 494/10 |
| 5,505,683 | 4/1996 | Geringer et al. | 494/12 |

FOREIGN PATENT DOCUMENTS

| | | |
|---|---|---|
| 0 592 242 A1 | 10/1993 | European Pat. Off. . |
| 0 654 669 A2 | 11/1993 | European Pat. Off. . |

Primary Examiner—David A. Reifsnyder
Attorney, Agent, or Firm—Theodore R. Furman; John K. Kilcoyne; Stuart E. Krieger

[57] ABSTRACT

An apparatus is provided for centrifuging and further automatically handling a container (110) for separating a component, such as fibrin monomer, from blood. The container (110) comprises a cylindrical member (27) and a piston displaceable in said cylindrical member, said piston comprising a tubular piston rod (8) extending through a top wall (73). The piston divides the cylindrical member (27) into a first chamber (70) positioned above said piston between said piston and the top wall (73), and a second chamber positioned below said piston. The top wall (73) of the container comprises an extension (90) defining a circumferential slit surrounding the outer side of the piston rod (8), whereby one end of said slit communicates in the axial direction with the first chamber. In addition, the first chamber communicates through a plurality of channels with the second chamber. The apparatus according to the invention comprises a supporting turntable (101) with means for releasably retaining the cylindrical member (27), said supporting turntable being connected to a first activating means (105) for rotating said supporting turntable (101) with the container (110) about the central axis thereof, as well as a rotatably journalled piston activating mechanism (113, 118) adapted to activate the piston (55) by means of a second activating means (115). The apparatus comprises an optical blood cell detector (130) which is adapted to emit a light beam obliquely towards the piston rod (8) through the extension (90) of the top wall (73) and the slit (91), and which comprises a detecting means for observing the intensity of the reflected light beam. The apparatus further comprises a control means (131) for controlling the piston activating mechanism (113, 118) in response to the measurements of the detecting means.

1 Claim, 3 Drawing Sheets

APPARATUS FOR SEPARATING A BLOOD COMPONENT FROM BLOOD PLASMA

This application claims benefit of U.S. provisional application No. 60/034,055, filed Jan. 8, 1997.

FIELD OF THE INVENTION

The present invention relates to methods and apparatus for separating blood into plasma and cellular components using a centrifuge. The invention is more particularly concerned with the use of a cylindrical separation container rotated in the centrifuge about its longitudinal axis and optical sensing means to control the content of cellular components within the separated plasma.

BACKGROUND ART

WO96/16714 discloses a container for separating a blood component, e.g., fibrin monomer, from blood by a centrifugation about a vertical axis. The first major step in such a process using this type of device is the centrifugal separation of blood into plasma and cellular fractions as described below. This container comprises a first annular chamber defined by an outer cylindrical wall and an inner cylindrical wall, both walls extending coaxially about a common axis, as well as by a top wall and a bottom wall, where the bottom wall is formed by a piston displaceable within the first chamber. The piston is activated by a piston rod, the outer surface of which provides the inner cylindrical wall. The piston rod extends outwardly through the top wall and is surrounded by a neck-like extension of the top wall. A slit, which is preferably annular, is provided between the extension and the piston rod. The container comprises furthermore a second chamber accommodated below the first chamber and communicating with the end of the said slit opposite the first chamber through a first conduit. The second chamber is defined by the outer cylindrical wall, the bottom wall of the first chamber, and by a second bottom wall. In use a blood sample is fed into the first chamber. Then the container is placed in a centrifuge apparatus and subjected to a centrifugation and activation of the piston. As a result, the blood in the first chamber is separated into a plasma fraction and a remaining portion of blood containing red and white blood cells. This second chamber serves as a reaction chamber for receiving plasma from the first chamber through the slit and the first conduit and for converting the fibrinogen content of the plasma into a non-cross-linked fibrin polymer by addition of a suitable enzyme. Centrifugation provides that the non-crosslinked fibrin polymer is separated from the plasma, and that it is deposited on the outer wall of the reaction chamber. When the piston is subsequently actuated, the remaining plasma is removed from the reaction chamber. Therefore, a solvent is added for dissolving the non-cross-linked fibrin polymer. The transferring of the plasma fraction of the blood from the first chamber to the second chamber through the slit and the first conduit must be carefully observed so that nothing of the remaining portion of blood containing the red blood cells is transferred to the second chamber.

BRIEF DESCRIPTION OF THE INVENTION

The object of the invention is to provide an apparatus allowing a control of the transfer of plasma to the second chamber in such a manner that the transfer of plasma is stopped as soon as red blood cells are present in the slit.

In satisfaction of the foregoing object there is provided an apparatus which according to the invention comprises an optical blood cell detector which is adapted to emit a light beam obliquely towards the piston rod through the extension of the top wall and the slit, and which comprises a detecting means for observing the intensity of the reflected light beam, and where the apparatus further comprises a control means for controlling the piston activating mechanism in response to the measurements of the detecting means. A continuous observation of the light beams reflected from the piston rod has the effect that the detector immediately registers a drop in the intensity of the reflected light beams, said drop being caused by red blood cells penetrating into the slit. When the detector registers a drop in the intensity, the movement of the piston is immediately stopped through the control means.

BRIEF DESCRIPTION OF THE DRAWING

The invention is described in greater detail below with reference to the accompanying drawing, in which.

DESCRIPTION OF A PREFERRED EMBODIMENT OF THE PRESENT INVENTION

The present invention provides a remarkably accurate apparatus and method for ensuring that a separated plasma sample is substantially free of cellular blood components, e.g., red and/or white blood cells. This can be accomplished during high speed centrifugation, e.g., at rotational speeds over 5000 RPM. The apparatus comprises two chamber in a centrifugal container; a first container for centrifugal separation into plasma and cellular fractions and a second chamber for receiving the plasma fraction. Transfer is preferably accomplished by action of the displacement of a piston in the first chamber to force the plasma fraction only, through a conduit means in proximity to a detecting means comprising a light beam and light sensor arranged to monitor material passing through the conduit means. The conduit means needs to include an outer light transmissive (at least to the detecting light beam) wall and an inner light reflective (at least at the angle of incidence of the detecting light beam) surface. As described below, an extending neck-portion of the centrifugal container is the outer light transmissive wall and the piston shaft is the inner reflective surface. The action of the piston is preferably responsive to the detecting means such that upon detection of a blood cell in the conduit means the piston motion and corresponding plasma transfer from the first to the second chamber is ceased.

The present invention also includes enhanced methods for preparing blood component compositions, e.g., fibrin monomer solutions, free of blood cells.

The present invention is hereafter described with regard to specific preferred apparatus and methods but is understood to be useful in variously modified ways without departing from the scope of the invention.

Figure 1:
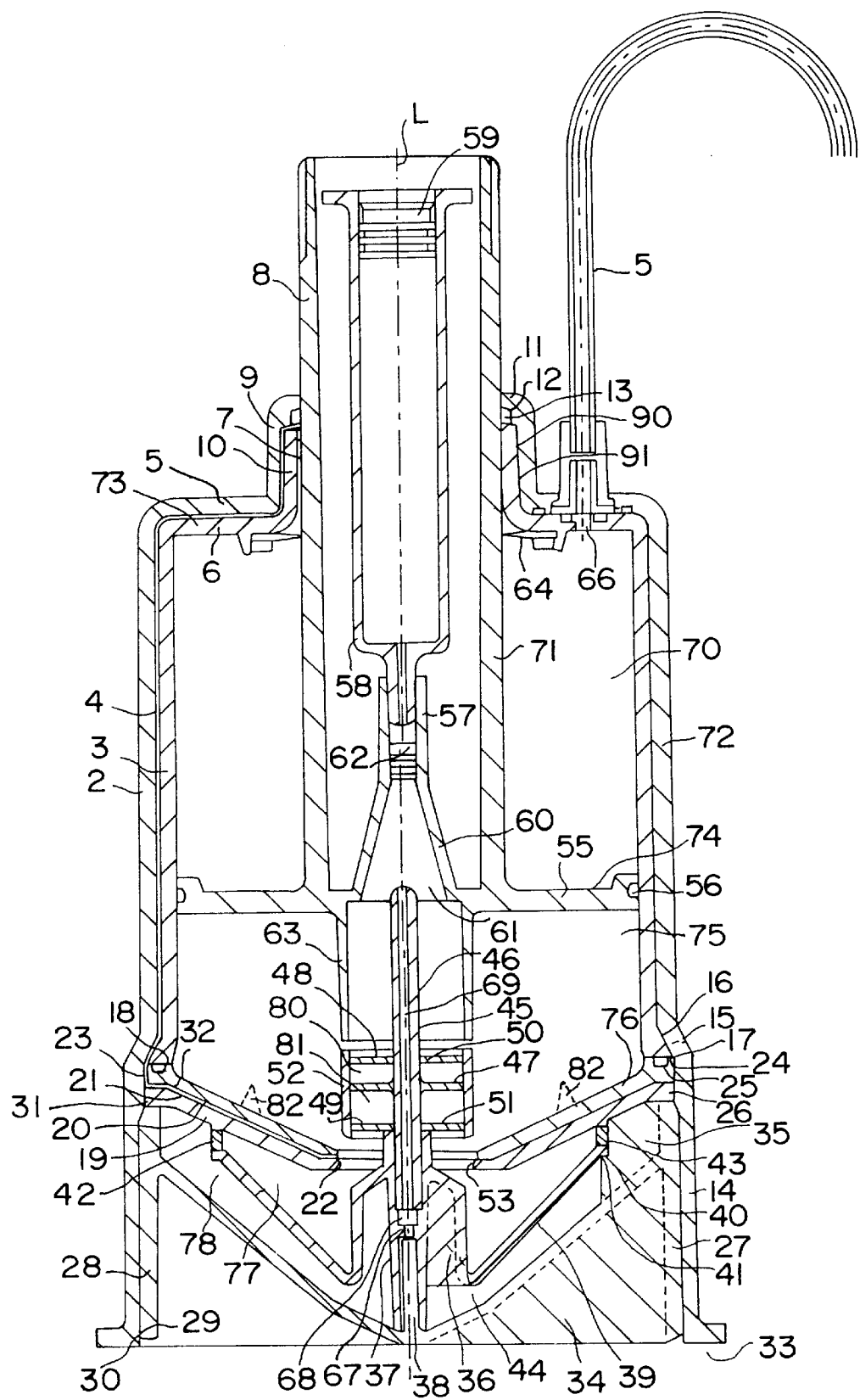
FIG. 1 is an axial sectional view of a prior art container for separating fibrin monomer from blood plasma.
Figure 2:
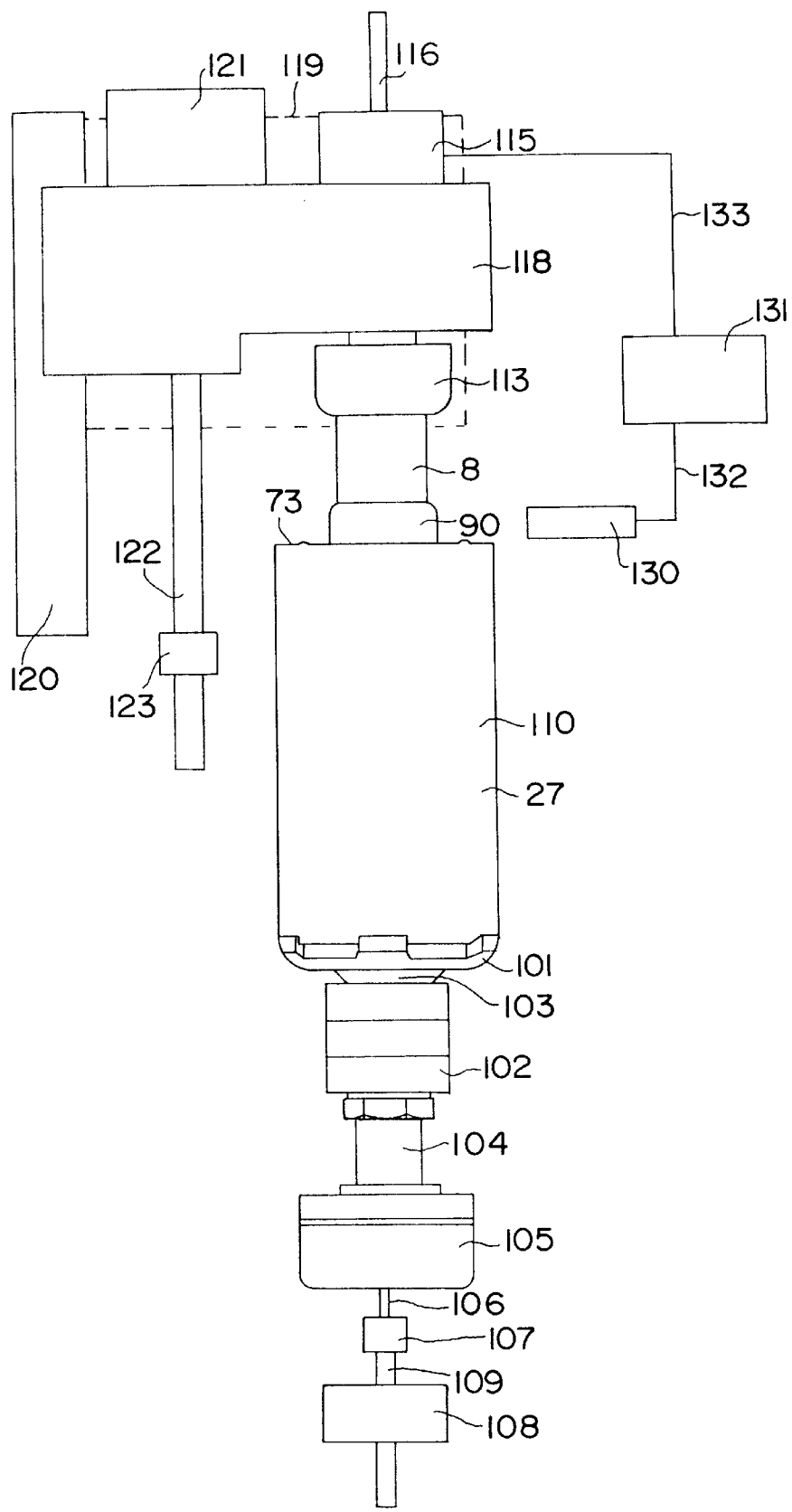
FIG. 2 is a diagrammatic view of an apparatus according to the invention during the handling of a container of the type shown in FIG. 1.

The container of FIG. 1 is known from the above WO 96/16714 and is built of parts substantially presenting rotation symmetry and implying that the container can be placed in a centrifuge apparatus shown in FIG. 2 so as to be centrifuged about a central axis 1. The container comprises an outer container part 2 and an inner container part 3 being such that they completely fit into each other and everywhere closely abut one another apart from the portion where an axially extending intermediary channel 4 is provided. The channel 4 is provided by a groove shaped in the inner container part 3. The two container parts 2 and 3 comprise their respective bottoms 5 and 6, respectively, said bottoms defining a central opening 7 allowing passage of a piston rod 8. About the opening 7, the two container parts comprise axially extending portions 9 and 10, respectively, which extend closely to the hollow piston rod 8 in a direction away from the interior of the container parts. The outer container part 2 abuts the hollow piston rod along a short radially extending flange 11 provided with a recess 12 receiving a sealing ring 13.

As illustrated in FIG. 1, the channel 4 continues between the inner and the outer container part all the way from the outer cylindrical walls of said inner and the outer container part along the bottoms 5, 6 and the axial portions 9 and 10 to the opening immediately below the sealing ring 13 in the opening 7. The axial portion 10 of the inner container part 3 abutting the opening 7 is dimensioned such that a narrow, but free passage exists to the interior of the container parts 2 and 3 about the hollow piston rod 8.

The outer container part 2 comprises a cylindrical portion of a uniform diameter, cf. FIG. 1. Downwardly, when seen relative to the drawing, this portion continues into a cylindrical portion 14 of a slightly larger diameter through a short transition portion 15 forming a frusto-conical inner surface 16. The inner container part 3 ends at the location where the transition portion 15 of the outer container part 2 continues into the cylindrical portion 14 of a larger diameter. The lower end of the inner container part 3 comprises an outer surface 17 of a frusto-conical form matching the form of the frusto-conical surface 16 on the inner side of the outer container part 2. An outer and an inner annular disk 19 and 20, respectively, are provided immediately below the lower end of the inner container part 3, which ends in a radial surface 18. These disks closely abut one another apart from the fact that they define therebetween a channel 21 extending in an axial plane from a central opening 22 and forwards to the inner side of the outer container part 2, where the channel 21 communicates with the channel 4 between the outer container part 2 and the inner container part 3 through an axially extending portion 23. The channel 21 and the axially extending portion 23 are suitably provided by means of a groove in the side of the inner disk 20 facing the outer disk 19. The two disks 19 and 20 are shaped with such an oblique course that they comprise substantially inner and outer frusto-conical surfaces and thereby incline downwards towards the central opening 22 in a direction away from the opening 7 of the hollow piston rod 8 in the outer container part 2 and the inner container part 3. FIG. 1 also shows that the inner disk 20 comprises a radial surface 24 abutting the adjacent radial surface 18 on the inner container part 3. The radial surface 24 of the inner disk 20 is provided with a recess 25 for receiving a sealing ring 26.

The two disks 19 and 20 are maintained in position in abutment against the radial surface 18 of the inner container part 3 by means of a cover 17 closing the outer container part 2 in the downward direction. This cover 17 comprises a circumferential sleeve-shaped portion 28 adapted to closely abut the inner side of the outer container part 2, to which it is secured in a suitable manner, such as by way of a snap-action by engagement between a circumferential rib 29 on the outer side of the sleeve 28 and a corresponding circumferential groove 30 on the inner side of the outer container part 2. A sealing connection is ensured by means of a sealing ring 31 in a circumferential recess 32 at the outer periphery of the outer disk 19. The cover 27 comprises furthermore a relatively thin wall 32 adapted to form the lower bottom of the container in the position shown in FIG. 1. This wall 32 extends substantially along a course parallel to the outer and the inner disk 19 and 20 in such a manner that the wall 32 extends from the inner side of the sleeve 27 in a portion adjacent the disks 19 and 20 and downwards towards a portion substantially on a level with the lower rim 33 of the outer container part 2. In order to reinforce this relatively thin wall 32, a reinforcing radial rib 34 is provided at regular intervals, only one of said ribs appearing from FIG. 1. This rib 34 is shaped partly with a portion placed outside the wall 32 and partly with a portion placed inside said wall 32, cf. FIG. 1. The latter inside portion is designated the reference numeral 35 and is shaped such that it abuts the bottom side of the outer disk 19 with the result that it assists in maintaining the disks 19 and 20 in a reliable position.

A partition means 36 is squeezed between the outer disk 19 and the cover 27. This partition means 36 comprises a central pipe length 37. This pipe length is mounted on a pin 38 projecting axially inwards and being shaped integral with the wall 32 of the cover 27. This pipe length 37 is shaped integral with a circumferential wall disk 39 extending outwardly from the pipe length 37 in such a manner that initially it inclines slightly downwards towards the wall 32 of the cover 27 whereafter it extends along a short axial course so as to continue into a course extending substantially parallel to the wall 32 of the cover. The wall disk 39 ends in a short radially extending periphery 40 resting on a shoulder 41 on the rib portions 35 on the cover 27. An annular filter unit 42 is squeezed between the outer periphery 40 of the wall disk 39 and the bottom side of the outer disk 19. This annular filter unit 42 abuts a substantially radially shaped surface 43 on the adjacent outer side of the outer disk 19.

In order to ensure a stability in the partition means 36, reinforcing radial ribs designated the reference numeral 44 are furthermore accommodated between the pipe length 37 and the wall disk 39.

A capsule designated the general reference numeral 45 is secured in the end opposite the cover 27 of the pipe length 37 of the partition means 36. This capsule comprises an elongated pipe length 46 shaped integral with a radial disk 47 and carrying two additional radial and annular disks 48 and 49. These radial disks 48 and 49 are secured by way of interference fit on their respective side of the fixed disk 47. The loose disks 48 and 49 are accommodated at their respective distance from the fixed ring 47 by means of circumferential shoulders 50 and 51, respectively, on the pipe length 46. The three disks 47, 48, and 49 are all of the same outer diameter and carry along their respective peripheries a circumferential, displaceably mounted sleeve 52.

As illustrated in the drawing, the lower disk 49 abuts the upper end of the pipe length 37 of the partition means 36, whereby the position of the capsule 45 in the axial direction is determined. This position is furthermore determined in such a manner that when displaced in the axial direction the displaceable sleeve 52 of the capsule enters a sealing engagement by its lower end, cf. the drawing, with the innermost edge 53 on the outer disk 19 in the central opening 22. In this position of the sleeve 52, a communication still exists between the space inside the inner disk 20 surrounding the sleeve 52 and the inlet opening to the channel 21 between the outer disk 19 and the inner disk 20. The axial length of the displaceable sleeve 52 is adapted such that the engagement with the outer disk 20 occurs before the upper end of the sleeve 52, cf. the drawing, disengages the fixed ring 47 during the axial downward displacement of said sleeve 52. The inner diameter of the sleeve 52 is also adapted to the outer diameter of the axially extending portion of the wall disk 39 of the partition means 36 in such a manner that a continued downward displacement of the sleeve 52 towards the cover 27 causes said sleeve 52 to fixedly engage the partition means 36 once it has disengaged the outer disk 19. The length of the axial portion of the partition means 36 corresponds also to the axial length of the sleeve 52 in such a manner that said sleeve 52 in the lowermost position is substantially completely received by the partition means 36.

As illustrated in the drawing, the hollow piston rod 8 comprises a circumferential piston 55 inside the outer container part 2 and the inner container part 3, said piston 55 sealingly engaging the inner side of the inner container part 3 through a sealing ring 56.

A Luer-coupling 57 is shaped inside the hollow piston rod for receiving a conventional syringe 58 with a piston-acting plug 59 for acting on the content of the syringe 58. The coupling 57 is shaped substantially as a pipe length communicating with a central opening 61 in the piston 55 through a frusto-conical portion 60. The pipe length 57 is provided with a radially inwardly projecting web 62 for directing the fluid leaving the syringe 58 away from an axial path and thereby round the elongated pipe length 46 therebelow inside the capsule 45. The latter pipe length 46 is of such a length and such dimensions that it can sealingly engage the pipe length 57 inside the hollow piston rod 8 when the piston 55 is in its lowermost position near the cover 27. In order to promote the above sealing connecting, the inner side of the pipe length 57 is formed with a gradually decreasing diameter at the end adjacent the piston 55.

An axially projecting skirt 63 is formed integral with the piston 55 about the central opening 61 of said piston. This skirt 63 is shaped with such a diameter and such a length that by a suitable displacement of the piston 55 it can activate the above displacement of the displaceable sleeve 52 of the capsule 45 into the said positions in which it engages the inner rim 53 of the central opening 22 through the two disks 19 and 20 followed by an engagement of the partition means 36.

A resilient, annular lip sealing means 64 is as indicated secured about the hollow piston at the top inside the container parts 2 and 3, cf. FIG. 1. This lip sealing means 64 is adapted to prevent an undesired passage of fluid from the interior of the container parts 2 and 3 to the channel 4, but it allows passage of fluid when a force is applied through the piston 55.

As indicated at the top of FIG. 1, a connection is provided to a hose 65 through an opening 66 in the outer and the inner container part 2 and 3, respectively. This connection is known and therefore not shown in greater detail, but it allows an interruption of the connection to the hose when desired. In addition, an air-escape opening with a suitable filter is provided in a conventional manner and therefore neither shown nor described in greater detail.

A passage 69 is provided from the area between the partition means 36 and the cover 27 and all the way upwards through the interior of the pipe length 37 of the partition means 36 and through the interior of the pipe length 46 of the capsule 45. This passage 69 allows a transfer of fluid to the syringe 58 from said area when the latter pipe length 46 is coupled to the pipe length 57 in the interior of the piston rod 8. The passage 66 is provided at the lowermost portion of the pin 38 in the cover 27 by said pin 38 being shaped with a plane, axial surface, said pin being of a substantially circular cross section. As a result, a space is provided between the pin and the adjacent portion of the inner side of the pipe length 37. An area 67 is provided immediately above the pin 38 where the partition means 36 presents a slightly reduced inner diameter. In this manner it is possible to place a small filter 68 immediately above the said area, cf. FIG. 1, whereby the fluid must pass said filter before it enters the pipe length 46 of the capsule 45.

The described container comprises a first annular chamber 70 defined inwardly by the hollow piston 8 forming a cylindrical inner wall 71, and outwardly by a cylindrical outer wall 27 formed by the outer container part 2 and the inner container part 3. When in the conventional use position, cf. FIG. 1, the annular chamber 70 is upwardly defined by a top wall 73 formed by the bottoms 5 and 6, respectively, of the outer container part 2 and the inner container part 3. The axially extending portions 9 and 10 of the container part 2 and 3 provide an extension 90 surrounding the piston rod 8. An annular slit 91 is defined between the extension 90 and the piston rod 8, and through this annular slit 90, the annular chamber 70 communicates with the channels 4 and 21 extending into the second chamber 75. Downwardly, the annular chamber 70 is defined by a bottom wall 74 formed by the piston 55. A second chamber 75 is defined below the piston 55, said second chamber outwardly being defined by the same cylindrical outer wall 72 as the first chamber 70. Downwardly, the second chamber 75 is defined by a second bottom wall 76 formed by the outer disk 19 and the inner disk 20. The capsule 45 is centrally accommodated in the interior of the second chamber 75. A third chamber 77 is provided below the said second bottom wall 76, and this third chamber 77 is defined by the partition means 36 and the annular filter unit 42. In addition, this third chamber 77 communicates with the second chamber 75 through the passage formed by the central opening 22 in the outer disk 19 and the inner disk 20. Finally, a fourth chamber 78 is provided below the partition means 36, said fourth chamber 78 being defined downwardly by the wall 32 of the cover 27 and furthermore by portions of the sleeve 28 of the cover 27 and the bottom side of the outer disk 19.

As described above, the container in question is primarily suited for separation of a component, such as fibrin monomer from blood, and for this purpose the second chamber 75, and preferably the upper chamber 80 of the capsule 46, is in advance filled with a suitable enzyme, such as batroxobin.

As is understood from EP-PS No. 592,242, any thrombin-like enzyme can be employed. Such enzymes include thrombin itself or any other material with a similar activity, such as Ancrod, Acutin, Venyyme, Asperase, Botropase, Crotabase, Flavorxobin, Gabonase, and the preferred Batroxobin. Batroxobin can be chemically bound to biotin, which is a synthetic substance allowing the batroxobin to be captured in a conventionally known manner by means of avidin in an avidin-agarose composition. Accordingly, avidin-agarose is found in the lowermost chamber 81 of the capsule. Both the biotin-batroxobin composition and the avidin-agarose composition are relatively easy to fill into the respective chambers 80 and 81 inside the capsule 45 before said capsule is placed inside the device.

Finally, a syringe 58 is arranged, said syringe containing a pH-4 buffer prepared from an acetate diluted with acetic acid. The syringe 58 is later used for receiving the desired fibrin monomer solution.

Another buffer known from the prior art can also be used. The redissolving buffer agent can be any acid buffer solution preferably those having a pH between 1 and 5. Suitable examples include acetic acid, succinic acid, glucuronic acid, cysteic acid, crotonic acid, itaconic acid, glutonic acid, formic acid, aspartic acid, adipic acid, and salts of any of these. Succinic acid, aspartic acid, adipic acid, and salts of acetic acid, e.g. sodium acetate are preferred. Also, the solubilization may also be carried out at a neutral pH by means of a chaotropic agent. Suitable agents include urea, sodium bromide, guanidine hydrochloride, KCNS, potassium iodide and potassium-bromide. Concentrations and volumes of such acid buffer or such chaotropic agent are as described in EP-PS No. 592,242.

During or immediately after the supply of blood, the piston rod 8 is pushed so far into the interior of the container that the displaceable sleeve 52 of the capsule 45 is moved downwards into a sealing engagement in the through passage through the bottom wall 76 and to the second chamber 77. As a result, access is simultaneously opened to the biotin-batroxobin composition inside the uppermost chamber 80 of the capsule.

When the container is ready for use, a blood sample is fed into the first chamber through a needle not shown and the hose 65 in a conventional manner, said blood sample preferably being admixed an anticoagulant also in a conventional manner. During the feeding of the blood through the hose 65 and the opening 66 into the interior of the first chamber 70, air is removed from the chamber in a conventional manner. After the feeding of blood the hose 65 is removed, and the opening 66 is sealingly closed. Subsequently, the container with the blood is placed in a centrifuge apparatus which inter alia assists in sealingly compressing the various portions. The centrifuge apparatus is described further below and causes the container to rotate about the axis of rotation 1. As a result of the centrifuging, the blood is separated in the first chamber 70 into a plasma fraction settling radially inside the remaining portion of the blood, said remaining portion containing the red and the white blood cells. As described in EP-PS No. 592,242 the platelets can be present in either fraction, as desired, by varying the speed and time of centrifugation.

When the interface between the plasma and the remaining portion of the blood has been stabilized, i.e. when the separation is complete, a reduction of the volume of the first chamber 70 is initiated by the piston rod 8 and consequently the piston 55 being pulled out. As a result, first a possible inner layer of air passes through the channels 4 and 21 into the second chamber 75, and a further moving of the piston 55 implies that also the plasma passes to the second chamber 75. The movement of the piston 55 is stopped when the entire layer of plasma has been forced into the second chamber 75, i.e. when the interface between the plasma fraction and the remaining portion of the blood has reached the inner wall 71 of the first chamber 70, whereby red blood cells are recognized in the slit 91.

In the second chamber 75, the plasma fraction comes into contact with the enzyme batroxobin with the result that fibrin monomer, which polymerizes immediately to a non-crosslinked fibrin polymer, is released from the plasma fraction. This process is performed while the container is being continuously centrifuged with the result that fibrin polymer is efficiently separated from the remaining portion of the plasma fraction, said fibrin polymer being formed by the reaction of the biotin-batroxobin composition and settling as a viscous layer along the cylindrical outer wall 72. When this separation has been completed, the centrifuging is stopped whereby the remaining relatively fluid portion of the plasma fraction can easily be pressed back into the first chamber 70 by the piston 55 first being raised for transferring air from the first chamber 70 to the second chamber 75 followed by said piston 55 being pressed down. This transfer can be performed relatively easily and quickly before the viscous layer with fibrin polymer reaches the opening to the channel 21. Further measures can optionally be taken in order to prevent the viscous layer from reaching the inlet of the channel 21 too quickly, such as by providing a ring of upwardly projecting teeth 82 shown by dotted lines at the bottom 76.

Once the remaining portion of the plasma fraction has been expelled from the second chamber 75, the displaceable sleeve 52 of the capsule 45 is further displaced downwards in such a manner that access is allowed to the lowermost chamber 81. At the same time or in connection with the latter displacement of the sleeve, the plug or piston 59 of the syringe 58 is pressed completely downwards by means of a spindle acting from the outside in such a manner that the pH-4 buffer is transferred to the second chamber 75, which can be done while initiating a centrifugal agitation. The addition of the pH-4 buffer provides that fibrin polymer is dissolved therein, and the presence of the avidin-agarose composition in the lower chamber 81 inside the capsule 45 implies that the biotin-batroxobin composition is bound in a conventional manner by the avidin. A continued displacement of the piston 55 causes the displaceable sleeve 52 on the capsule 45 to engage the partition means 36 and to a disengage the bottom wall 76 with the result that a free access is provided to the third chamber 77. As a result, the contents of the second chamber 75 can flow freely downwards into the third chamber 77. Preferably, the redissolving is carried out during centrifugal agitation which involves centrifugation and a series of stop-and-start of forward/reverse agitation motions.

A continued centrifuging has the effect that the fibrin monomer solution can be separated in the third chamber through the annular filter unit 42 retaining the relatively large particles of agarose and the batroxobin bound thereto. When the fibrin monomer solution has passed into the lowermost fourth chamber 78 as a result of the above centrifuging, said centrifuging is stopped and the fibrin-l-solution is easily transferred to the syringe 58 by a renewed retraction of the piston 59, the uppermost end of the pipe length 46 of the capsule 45 engaging the pipe length 57 forming the connection with the syringe 58.

The described handling of the container shown in FIG. 1 is carried out in a centrifuge apparatus of the type diagrammatically shown in FIG. 2.

The apparatus shown in FIG. 2 comprises a supporting turntable 101 which is rotatably journalled in a housing not shown in greater detail by means of a ball bearing 102. The supporting turntable 101 is formed integral with a vertical driving shaft 103. The driving shaft is connected through a coupling 104 to a motor 105 causing the supporting turntable to follow a rotating movement about a vertical axis of rotation. An activating bar 106 is rotatably journalled coaxially with the axis of rotation inside the driving shaft 103 of the supporting turntable 101, said activating bar 106 being connected through a coupling 107 with a spindle motor 108 with a spindle 109 in such a manner that when the spindle motor 108 is activated the activating bar 106 can be displaced vertically upwardly or downwardly in order to engage or disengage a container 110 placed on the supporting turntable 101.

The container 110 is arranged on top of the supporting turntable, said container being of the type shown in FIG. 1. The piston 55 of the container 110 is driven by means of the tubular piston rod 8, cf. FIG. 1, projecting upwardly from the upper end of the container 110. The piston rod 8 is activated by means of a gripping means 113, which in turn is activated by means of a spindle motor 115 through a spindle 116 and an activating bar (not shown) integrally connected thereto. The spindle 116 driven by the motor 115 is also activating the piston 59, cf. FIG. 1, of the syringe 58 through the said activating bar.

The gripping means 113 is furthermore rotatably journalled in a housing 118 through a ball bearing. The housing 118 and the spindle motor 115 are secured to a common carrier indicated by means of dotted lines at the reference numeral 119. This carrier 119 is displaceably mounted on a rail 120 and caused to be vertically displaced thereon by means of a motor 121. The motor 121 co-operates through a ball spindle with a ball nut 123 stationarily secured in the apparatus in such a manner that a rotation of the ball spindle 122 by means of the motor 121 causes a movement of the carrier 119 and consequently of the gripping means 113 along the slide 20.

The transfer of plasma from the first chamber 70 to the second chamber 75, cf. FIG. 1, must be carefully observed in such a manner that red blood cells are not transferred to the second chamber in which they risk having a negative effect on the further preparation of fibrin monomer. The said observation is performed by means of an optical blood cell detector diagrammatically shown in FIG. 2 and designated the general reference numeral 130. The detector 130 comprises a light source which is adapted to emit a laser beam towards the piston rod 8 through the extension 90 of the container 110. The laser beam is directed into such an inclining path relative to the surface of the piston rod 8 that it is reflected from said piston rod 8. The detector 130 comprises furthermore a detecting means which is adapted to register the intensity of the reflected beam(s) and consequently of the changes therein, said changes indicating that blood cells are present in the slit 91, cf. FIG. 1, between the extension 90 and the piston rod 8.

In order to adjust the movement of the piston rod 8 in response to the above, the blood cell detector 130 is connected to a control means 131. At a signal from the blood cell detector 130 through a conduit 132, the control means 131 causes an immediate stop of the movement of the piston rod 8 when red blood cells are detected in the slit 91. The movement of the piston rod 8 is stopped at a signal from the control means 131 to the motor 115 through a conduit 133.

The accurate position of the light source and the detecting means of the blood cell detector 130 relative to one another and to the extension 90 of the container 110 is determined in a conventionally known manner by means of a computer-produced model (ray tracing model).

Figure 3:
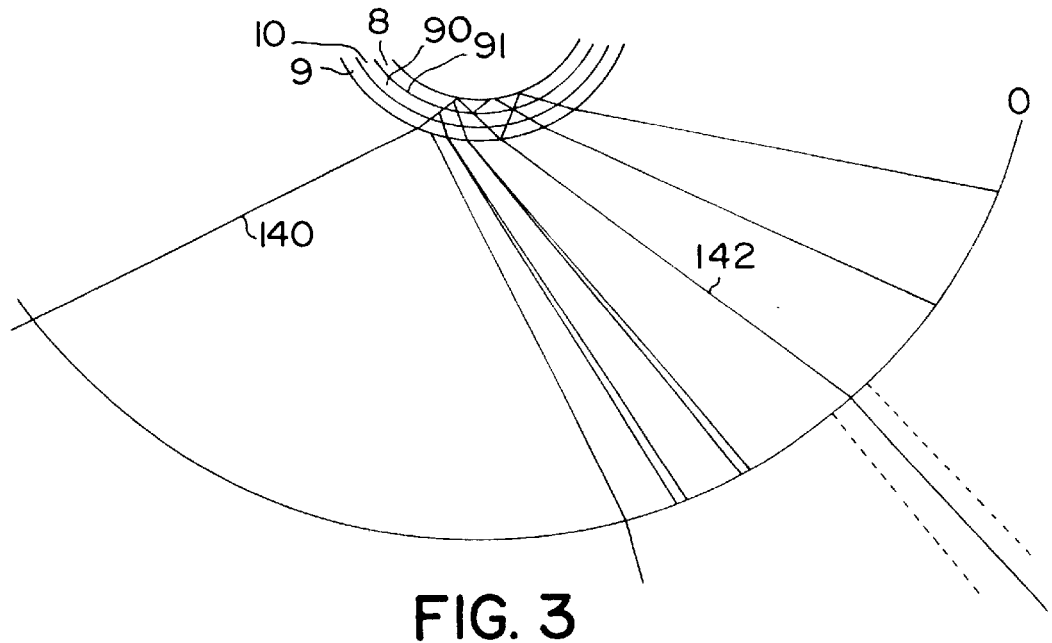
FIG. 3 illustrates a graphing of the path of light beams through an upper extension of the top wall of the container and the adjacent part of the wall of the piston rod as well as the intensity of the reflected beams when seen during the transfer of plasma from a first chamber to a second chamber in the container.
Figure 4:
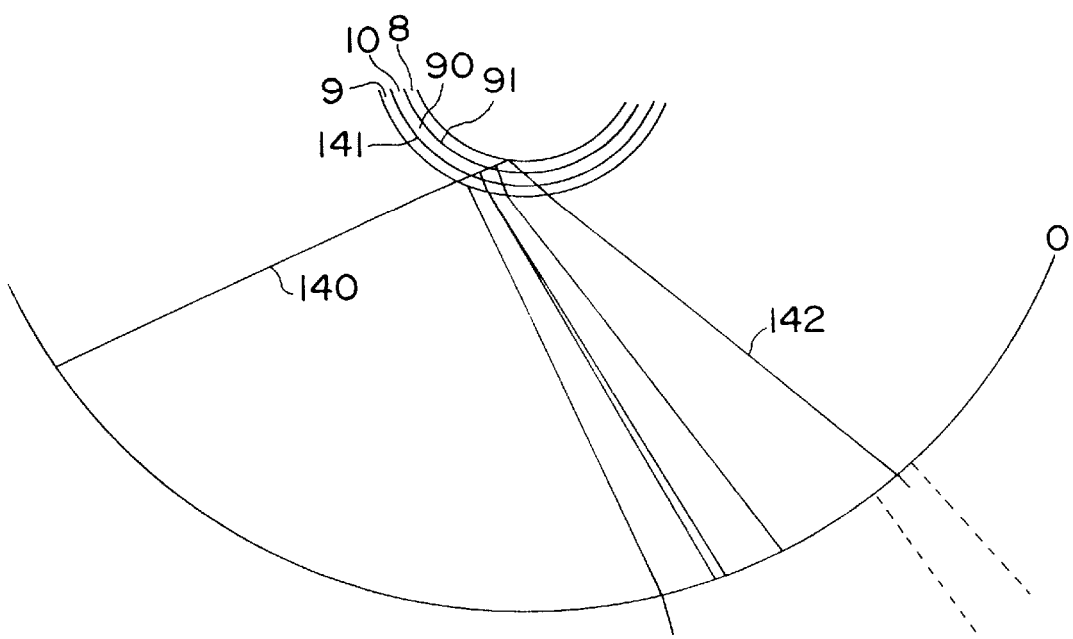
FIG. 4 shows the same as FIG. 3, but when red blood cells enter a slit surrounding the outer side of the piston rod.

FIGS. 3 and 4 are diagrammatic views of the path of the laser beam. The laser beam transmitted towards the container 110 is designated the general reference numeral 140. It hits the extension 90 of the container 110, and in sequence it subsequently passes through the axially extending portions 9 and 10 of the container parts 3 and 4, respectively, and the wall of the hollow piston rod 8. As a result, the laser beam 140 passes initially through a slit 141 between the axially extending portions 9 and 10 and subsequently through the slit 91 adjacent the piston rod 8. Everywhere, portions of the laser beam 140 are reflected, and especially at the transition from the plastic material to air. A suitable setting of the angle of incidence of the beam relative to the outermost surface of the extension 90 has the effect that the resulting reflection is strongest from the inner side of the piston rod, i.e. after the passage of the slit 91. Portions of the light beam reflected from the slit 91 are refracted several times, but the main beam exits in form of a beam at 142. The intensity of the latter as well as of other reflected beams indicated in the drawing in form of the length of the beam in a direction substantially radially outwards from a circular arc 0. The detecting means is arranged on the location where the strongest reflection exits so as to observe the intensity of said beam. The position of the detecting means in indicated in FIG. 1 by means of dotted lines.

FIG. 3 shows the reflection of the light beam 140 while plasma is transferred from the first chamber 70 and into the second chamber 71. The reflected light beam 142 is, as indicated, relatively strong.

FIG. 4 shows how the intensity of the reflected light beam 142 has dropped at the appearance of red blood cells in the slit 91. The use of the described apparatus renders it possible to achieve an instantaneous stop of the movement of the piston rod 8 in such a manner that red blood cells are not transferred to the second chamber 75.

The optical blood cell detector is of a conventionally known type, and for instance a photometer may be used.

The invention has been described with reference to a preferred embodiment. Many modifications can be carried out without thereby deviating from the scope of the invention.

We claim:

1. An apparatus for centrifuging and further automatically handling a container for separating fibrin monomer from blood, where the container comprises a cylindrical member and a piston displaceable in said cylindrical member said piston comprising a tubular piston rod extending through a top wall, and where the piston divides the cylindrical member into a first chamber positioned above said piston between said piston and the top wall, and a second chamber positioned below said piston and where the top wall of the container comprises an extension defining a circumferential slit surrounding an outer side of the piston rod, whereby one end of the slit communicates in an axial direction with the first chamber, and whereby said first chamber communicates through a plurality of channels with the second chamber, and where said apparatus comprises a supporting turntable with means for releasably retaining the cylindrical member, said supporting turntable being connected to a first activating means for rotating said supporting turntable with the container about a central axis thereof, as well as a rotatably journalled piston activating mechanism adapted to activate the piston by means of a second activating mechanism, the apparatus further comprising an optical blood cell detector which is adapted to emit a light beam obliquely towards the piston rod through the extension of the top wall and the slit, a detecting means for measuring the intensity of the reflected light beam, and a control means for controlling the piston activating mechanism in response to the measurements of the detecting means.

* * * * *